(12) United States Patent
Pinori et al.

(10) Patent No.: US 7,427,620 B2
(45) Date of Patent: Sep. 23, 2008

(54) AZOLE DERIVATIVE USEFUL AS ANTIFUNGAL AGENTS WITH REDUCED INTERACTION WITH METABOLIC CYTOCHROMES

(75) Inventors: Massimo Pinori, Paderno d'Adda Lecco (IT); Maria Lattanzio, Milan (IT); Daniela Modena, Milan (IT); Paolo Mascagni, Milan (IT)

(73) Assignee: Italfarmaco SPA, Milan (IT)

(*) Notice: Subject to any disclaimer, the term of this patent is extended or adjusted under 35 U.S.C. 154(b) by 362 days.

(21) Appl. No.: 10/576,194

(22) PCT Filed: Oct. 14, 2004

(86) PCT No.: PCT/EP2004/011667
§ 371 (c)(1), (2), (4) Date: Apr. 17, 2006

(87) PCT Pub. No.: WO2005/040156
PCT Pub. Date: May 6, 2005

(65) Prior Publication Data
US 2007/0129376 A1    Jun. 7, 2007

(30) Foreign Application Priority Data
Oct. 17, 2003   (IT)   .................. MI2003A2020

(51) Int. Cl.
*A61K 31/497* (2006.01)
*C07D 403/00* (2006.01)
*C07D 413/00* (2006.01)
*C07D 417/00* (2006.01)
*C07D 419/00* (2006.01)

(52) U.S. Cl. .................. 514/254.03; 514/254.07; 544/366; 544/367

(58) Field of Classification Search ............ 514/254.03, 514/254.07; 544/366, 367
See application file for complete search history.

(56) References Cited

FOREIGN PATENT DOCUMENTS

| | | |
|---|---|---|
| EP | 0 237 693 | 9/1987 |
| EP | 0 237 963 A | 9/1987 |
| EP | 0 237 963 A2 * | 12/1987 |
| EP | 0 958 289 A | 11/1999 |
| WO | WO 95/17407 | 6/1995 |
| WO | WO 98/00113 A | 1/1998 |
| WO | WO 98/34934 | 8/1998 |
| WO | WO 99/58529 | 11/1999 |
| WO | WO 01/74808 A1 | 10/2001 |

* cited by examiner

*Primary Examiner*—James O. Wilson
*Assistant Examiner*—Erich A Leeser
(74) *Attorney, Agent, or Firm*—Nixon & Vanderhye

(57) ABSTRACT

The present invention relates to novel compounds, of the general formula (I), the N-oxide forms thereof, the salts thereof with pharmaceutically acceptable acids and the stereochemical isomers thereof, which are useful as antifungal agents; to pharmaceutical compositions containing such compounds as the active ingredient; to methods for the production of said compounds and the associated pharmaceutical compositions.

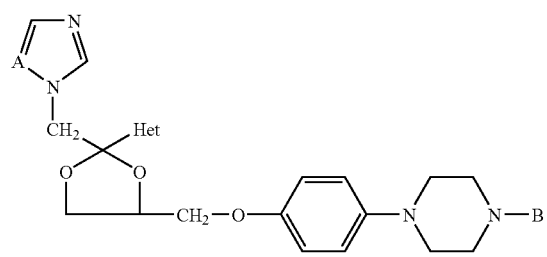

8 Claims, No Drawings

AZOLE DERIVATIVE USEFUL AS ANTIFUNGAL AGENTS WITH REDUCED INTERACTION WITH METABOLIC CYTOCHROMES

This application is the U.S. National Phase of International Application PCT/EP2004/011667, filed 14 Oct. 2004, which designated the U.S. PCT/EP2004/011667 claims priority to Italian Application No. MI2003A002020 filed 17 Oct. 2003. The entire content of these applications are incorporated herein by reference.

The present invention relates to novel compounds, of the general formula (I), the N-oxide forms thereof, the salts thereof with pharmaceutically acceptable acids and the stereochemical isomers thereof, which are useful as antifungal agents; to pharmaceutical compositions containing such compounds as the active ingredient; to methods for the production of said compounds and the associated pharmaceutical compositions.

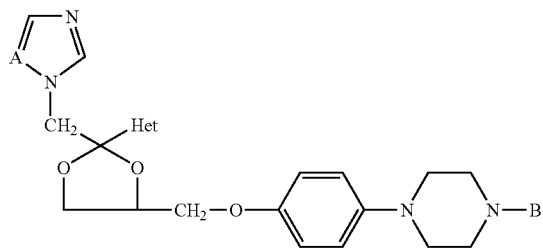

Formula (I)

PRIOR ART

Numerous 1H-imidazole and 1H-1,2,4-triazole derivatives have been described and used for their antifungal properties. In particular derivatives of the type 1-(1,3-dioxolan-2-yl)methyl-1H-imidazoles and 1H-1,2,4-triazoles have been described in U.S. Pat. No. 4,144,346, while others, of the type 1-(4-phenyl-1-piperazinyl-aryloxymethyl-1,3-dioxolan-2-yl)methyl-1H-imidazoles and 1H-1,2,4-triazoles, have been described in U.S. Pat. No. 4,267,179.

Itraconazole, one of the antifungal agents most widely used in clinical practice, belongs to this class of molecules; in itraconazole, as in other antifungal agents of this class, there is a dichlorophenyl (or difluorophenyl) residue attached to position 2 of the dioxolane ring.

We have now discovered a new class of antifungal molecules in which a heteroaromatic residue is attached to position 2 of the dioxolane ring; this new class of molecules, while retaining the antifungal properties of previous molecules, interacts to a lesser extent with some metabolic cytochromes; this characteristic is indicative of a -better toxicological profile and of reduced interaction with other drugs. Moreover, the molecules provided by the present invention have good solubility in water and may more readily be formulated and administered orally and/or parenterally.

DESCRIPTION OF THE INVENTION

The present invention provides novel 1H-imidazole and 1H-1,2,4-triazole derivatives having the formula

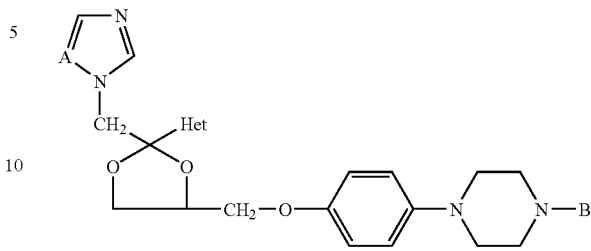

Formula (I)

the salts thereof with pharmaceutically acceptable acids, the N-oxide forms thereof and the stereochemical isomers thereof, where:

A is N or CH;

Het is an aromatic heterocyclic radical containing one or more O, N or S atoms, optionally substituted with one or more 5- or 6-membered aromatic rings; said radical may, for example, be selected from among: pyridines, pyridazines, pyrazines, pyrimidines, thiophenes, oxazoles, thioazoles, pyrroles, pyrazoles, imidazoles, triazoles and any corresponding fusion derivatives having two or more rings or with one or more benzene rings;

B is an alkanoic residue containing from 1 to 6 carbon atoms (for example formyl, acetyl, propanoyl etc.) or is a residue of the formula

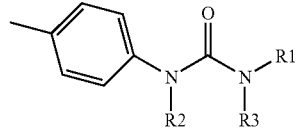

Formula (II)

where:

R1 is hydrogen or a linear or branched alkyl residue containing from 1 to 6 carbon atoms and optionally substituted in one or more positions by hydroxyl type groups;

R2 and R3, taken separately, may be hydrogen or an alkyl with 1-4 carbon atoms or, taken together, may be a divalent radical of the formula —CH═N—, —N═CH—, —CH═CH—, —CH$_2$—CH$_2$—.

Those compounds of the formula (I) where R1 is hydrogen may give rise to tautomeric forms, which also fall within the scope of the present invention.

Compounds of the formula (I) may furthermore exist in hydrated and/or solvated form and such forms also fall within the scope of the present invention.

The present invention also provides the use of the compounds of the formula (I), both as a mixture of stereochemical isomers and in the form of the individual isolated isomers as active ingredients alone or in combination with other medicines for the production of pharmaceutical compositions intended for the treatment of conditions of mycotic origin (such as for example vaginal candidiasis) by means of topical and/or systemic administration.

The compounds provided by the present invention may be prepared by joining intermediates of the formula (III),

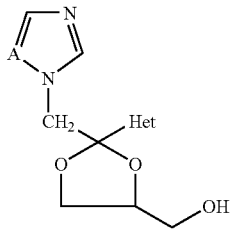

Formula (III)

where A and Het are defined as above, with intermediates of the formula (IV),

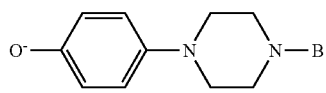

Formula (IV)

where B is defined as above.

The hydroxyl group of the intermediates (III) may be converted into an activated group (tosyl, mesyl, triflate etc.) by methods known to the person skilled in the art.

The intermediates of the formula (III) may be prepared using methods known to the person skilled in the art; for example, starting from the corresponding bromoacetyl heteroaromatic derivatives, the procedure described in scheme 1 shown below may be followed.

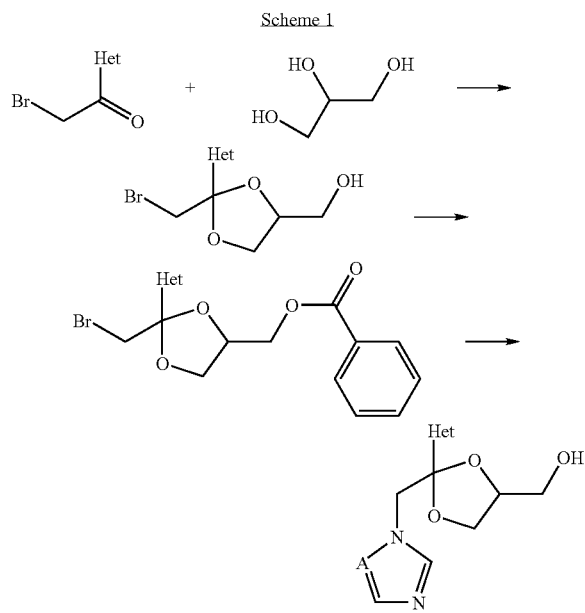

Scheme 1

Intermediates of the formula (IV) are commercially available, or may be prepared by means of known synthetic methods.

On the basis of the formula (I), it is obvious that the compounds provided by the present invention contain at least two asymmetric carbon atoms, specifically the atoms in positions 2 and 4 of the dioxolane ring; said compounds may accordingly exist in different stereoisomeric forms which, whether individually or as a mixture, fall within the scope of the present invention. With regard to the dioxolane ring, two regioisomeric forms may be distinguished, each comprising a pair of enantiomers which, in accordance with the rules stated in the C.A. Index Guide, section IV, page 85 (1972) are respectively denoted the cis form and the trans form. The two racemic forms may be obtained separately by using methods known to the person skilled in the art. Methods which may usefully be used include selective crystallisation and chromatographic separation. Such methods may also usefully be applied during the production of the intermediates of the formula (III), once the stereochemical configuration of the dioxolane ring has been established; in some cases, depending on the nature of the heterocyclic group, regioselective secondary reactions may also occur which result in the removal of one of the two forms. This occurs, for example, when the heterocyclic nucleus consists of 2-pyridine; in this case, during activation of the intermediate (III), the trans form is subjected to an intramolecular regioselective reaction which facilitates its removal from the reaction mixture (c.f. scheme 2).

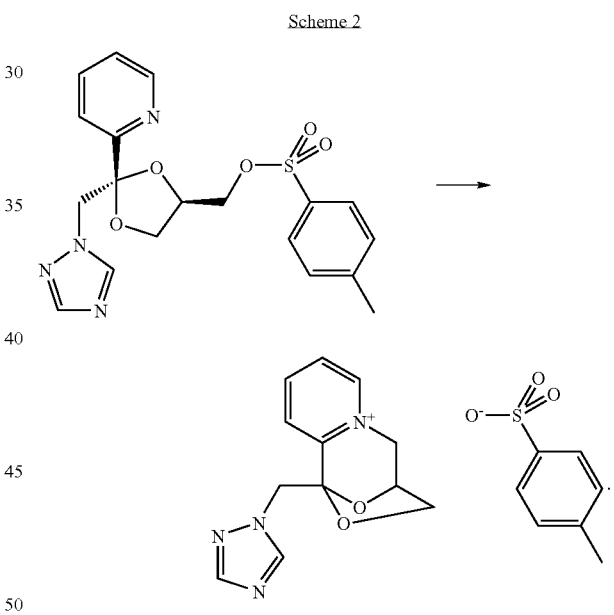

Scheme 2

The optical isomers of the two regioisomeric forms (cis(+), cis(−), trans(+) and trans(−)) may in turn be obtained separately, preferably as early as during preparation of the intermediates of the formula (III) by using methods known to the person skilled in the art.

The compounds of the formula (I) and the pharmaceutically acceptable salts thereof are valuable therapeutic agents for treating fungal and bacterial infections. These compounds have in fact demonstrated considerable antifungal activity, both in vitro and in in vivo, towards various species of fungi, such as *Candida albicans, Candida glabrata, Candida parapsilosis, Aspergillus fumigatus.*

Another positive characteristic of the compounds of the formula (I) concerns their limited activity in inhibiting various metabolic enzymes (for example the cytochromes CYP1A2, CYP2C9, CYP2C19, CYP2D6 and CYP3A4) which, in contrast, are frequently inhibited by other azole type antifungal agents. The inhibition of such enzymes in fact underlies various toxic effects and interactions with other drugs exhibited by some drugs in this class.

The data obtained in the experiments described below demonstrate the antifungal and antibacterial potency of some compounds of the formula (I) and their slight inhibition of the more significant cytochromes; these examples are merely intended to illustrate the usefulness of this class of compounds, but not to limit the scope of the present invention, whether with regard to the type of microorganisms which may effectively be combatted or with regard to the descriptive scope of the of the general formula (I).

formula (I) was measured by using specific substrates which become fluorescent as a result of the metabolic action of a particular cytochrome isoform. The individual isoenzymes (Gentest) and the respective substrates were incubated in 96 well plates in buffer containing NADH at 37° C. in the presence or absence of the compound under investigation. On completion of the experiment, the plates were read at the appropriate wavelengths in a "Fluoroskan Ascent" instrument, and the $IC_{50}$ values (minimum concentration to bring about 50% inhibition) were calculated. The degree of inhibition of each individual isoenzyme by known inhibitors was also assessed as a positive control.

Table no. 2 shows the $IC_{50}$ values ($\mu M$) obtained for some of the compounds of the invention.

TABLE NO. 2

| Cytochrome | CYP1A2 | CYP2C9 | CYP2C19 | CYP2D6 | CYP3A4 |
|---|---|---|---|---|---|
| Example 9 | >100 | 54.1 ± 5.2 | 40.7 ± 12.7 | >100 | 0.22 ± 0.05 |
| Example 11 | — | 64.2 ± 6.2 | 31.5 ± 3.9 | — | 0.70 ± 0.1 |
| Example 12 | — | 18.2 ± 0.3 | 10.9 ± 0.4 | — | 0.30 ± 0.1 |
| Example 13 | >100 | 27.2 ± 6.7 | 28.4 ± 8.8 | >100 | 0.46 ± 0.37 |
| Example 14 | >100 | 40.0 ± 11.2 | 27.9 ± 0.8 | >100 | 0.19 ± 0.08 |
| Example 15 | >100 | 26.1 ± 1.3 | 25.5 ± 4.3 | 84.0 ± 39.4 | 0.41 ± 0.13 |
| Example 16 | >100 | 37.5 ± 6.8 | 43.1 ± 15.0 | >100 | 0.29 ± 0.01 |
| Itraconazole | >100 | 1.6 ± 0.2 | 0.20 ± 0.06 | >100 | <0.05 |

Experiment A: Antifungal Activity of Compounds of the Formula (I)

The antifungal activity of the compounds of the formula (I) was determined using various strains of yeast and filamentous fungi. The $IC_{50}$ value (minimum concentration to bring about 50% inhibition) was determined using the liquid phase microdilution method as specified in documents M27 (1997) and M38-P (1998) from NCCLS (National Committee for Clinical Laboratory Standards). Table no. 1 shows $IC_{50}$ values (mg/ml) for some compounds of the invention.

TABLE NO. 1

| | Fungus | | | | |
|---|---|---|---|---|---|
| Strain | Candida albicans 21 | Candida glabrata gen-45 02-0902 | Candida parapsilosis ATCC22019 | Aspergillus fumigatus 34 99-2135 | |
| Example 9 | 39 | ≦0.03 | 1 | ≦0.03 | 0.25 | 0.25 |
| Example 10 | 39 | — | — | — | 8 | — |
| Example 13 | — | ≦0.03 | 1 | ≦0.03 | — | 0.25 |
| Example 14 | — | ≦0.03 | 2 | 0.06 | — | 0.5 |
| Example 15 | — | ≦0.03 | 0.25 | ≦0.03 | — | 0.12 |
| Example 16 | — | ≦0.03 | 0.5 | 0.06 | — | 0.25 |
| Example 17 | 38 | — | — | — | >64 | — |
| Example 18 | 78 | — | — | — | — | — |
| Itraconazole | >128 | ≦0.03 | 0.5 | 0.12 | 1 | 0.25 |

Experiment B: Inhibition of Human Cytochromes by Compounds of the Formula (I)

Inhibition of the enzymatic activity of the most significant isoforms of human cytochromes by the compounds of the Experiment C: Study of the Efficacy of Compounds of the Formula (I) in a Mouse Model of Systemic Candidiasis.

Immunocompetent CD1 mice (approx. 20 g) were inoculated with a strain of *Candida albicans* of clinical origin, which had previously been investigated for its in vitro susceptibility to itraconazole (NCCLS standard method) and for its $LD_{50}$ in mice.

The *C. albicans* isolate was cultured for 24 h in yeast dextrose broth. The blastospores were recovered by centrifugation, repeatedly washed in sterile saline solution and the inoculum adjusted to the desired concentration. The inoculum was verified by a subsequent count of CFU/ml on Sabouraud plates.

The mice were then inoculated intravenously (0.2 ml/mouse).

24 hours after inoculation with *C. albicans*, the animals were randomised into the following treatment groups (10 mice/group):

1. Itraconazole: 50 mg/kg/day (two 25 mg/kg treatments twice daily at 12 hour intervals)
2. Compound under investigation: 50 mg/kg/day (two 25 mg/kg treatments twice daily at 12 hour intervals)
3. Compound under investigation; 10 mg/kg/day (two 5 mg/kg treatments twice daily at 12 hour intervals)
4. Control (placebo)

The compounds were administered orally (suspension in PEG 200, 0.2 ml/mouse) for 10 consecutive days and the animals were observed until day 30. The survival curves between the various treatment groups and between these groups and the control group were evaluated using the Kaplan-Meier method.

TABLE NO. 3

| Treatment | Survival: | |
|---|---|---|
| | Average survival (days) ± S.D. | Surviving mice 21 days after infection |
| Placebo | 5.3 ± 0.4 | 0% |
| Example 9 (10 mg) | 6.6 ± 0.8 | 0% |
| Example 9 (50 mg) | 9.1 ± 1.5 | 10% |
| Itraconazole (50 mg) | 9.2 ± 1.1 | 0% |

EXAMPLES

The following Examples are intended to illustrate the scope of the present invention and should not be considered to limit it in any way.

(A) Preparation of the Intermediates of the Formula (III)

Example No. 1

A) Synthesis of 2-bromoacetyl-pyridine hydrobromide 100 g of 2-acetylpyridine were dissolved in 366 ml of 33% hydrobromic acid in acetic acid; the solution was heated to 40° C. and a solution of 264 g of pyridinium tribromide in 500 ml of acetic acid was added. The mixture was kept at 40° C. overnight.

The reaction mixture was cooled and the precipitate filtered out and washed with 200 ml of acetic acid. The precipitate was resuspended in 400 ml of THF, then filtered out and dried, giving rise to 200 g of 2-bromoacetyl-pyridine hydrobromide (yield 87%).

B) Synthesis of 2-(pyridin-2-yl)-2-bromomethyl-4-hydroxymethyl-1,3-dioxolane (cis/trans)

316 ml of glycerol were dissolved in 2 l of toluene and 13.6 g of p-toluenesulfonic acid and 195 g of 2-bromoacetyl-pyridine hydrobromide were added to this solution.

The reaction mixture was refluxed for 24 hours, with removal of the water present in the azeotrope. Once the mixture had cooled to ambient temperature, 2 l of 5% NaHCO$_3$ were added, the two-phase mixture was stirred for 5 minutes and the phases were then separated. The aqueous phase was extracted six times with 600 ml of toluene, the organic phases were combined, dehydrated with Na$_2$SO$_4$, and evaporated to dryness under reduced pressure, giving rise to 80 g of (cis/trans)-2-(pyridin-2-yl)-2-bromomethyl-4-hydroxymethyl-1,3-dioxolane (yield 42%).

C) Synthesis of cis(±)-2-(pyridin-2-yl)-2-bromomethyl-4-benzoxymethyl-1,3-dioxolane 80 g of (cis/trans)-2-(pyridin-2-yl)-2-bromomethyl-4-hydroxymethyl-1,3-dioxolane, obtained in the previous section, and 47 ml of pyridine were dissolved in 800 ml of methylene chloride; 34 ml of benzoyl chloride dissolved in 200 ml of methylene chloride were added to the solution, which was cooled in an ice bath. Once the addition was complete, the reaction mixture was kept at ambient temperature overnight, then was washed twice with 500 ml of 5% NaHCO$_3$. The organic phase was dehydrated with Na$_2$SO$_4$ and evaporated to dryness.

The crude product was purified on a silica gel column using an ethyl acetate in n-hexane gradient (from 10 to 40%). 22.1 g of cis(±)-2-(pyridin-2-yl)-2-bromomethyl-4-benzoxymethyl-1,3-dioxolane were obtained (yield 19.9%). 41.2 g of "trans" product were also obtained to give a total of 63.3 g of 2-(pyridin-2-yl)-2-bromomethyl-4-benzoxymethyl-1,3-dioxolane (overall yield 57%).

TLC (hexane/ethyl acetate; 1:1 vol./vol.): Rf for cis regioisomer=0.55, Rf for trans regioisomer=0.64

D) Synthesis of cis(±)-2-(pyridin-2-yl)-2-(1,2,4-triazol-1-yl-methyl)-4-hydroxymethyl-1,3-dioxolane 6 g of cis(±)-2-(pyridin-2-yl)-2-bromomethyl-4-benzoxymethyl-1,3-dioxolane, obtained in the previous section, were dissolved in 100 ml of DMF, 3.4 g of 1,2,4-triazole potassium salt were added to the solution and the mixture was heated to 130° C. for 24 hours. The solvent was removed under reduced pressure, the residue was diluted with 130 ml of THF/water (5:1; vol./vol.) and 20.4 ml of 32% NaOH and the mixture was refluxed for 3 hours. Once the reaction mixture had cooled, the phases present were separated and the basic aqueous phase was extracted three times with 20 ml of THF. The combined organic phases were dehydrated and evaporated. The residue obtained was redissolved with 200 ml of THF and undissolved solids were removed by filtration.

The solution was evaporated and the residue was purified on a silica gel column, elution being carried out with a mixture of ethyl acetate/methanol (85:15; vol./vol.); The secondary product cis(±)-2-(pyridin-2-yl)-2-(1,2,4-triazolyl-4-yl-methyl)-4-hydroxymethyl-1,3-dioxolane (TLC in AcOEt/MeOH 8/2; Rf=0.12) was removed in this purification step and 2.98 g of cis(±)-2-(pyridin-2-yl)-2-(1,2,4-triazol-1-yl-methyl)-4-hydroxymethyl-1,3-dioxolane (TLC in AcOEt/MeOH 8/2; Rf=0.27) were obtained (yield 71%).

$^1$H NMR (200 MHz):

δ (CDCl$_3$)=8.68 (d 1H); 8.1 (s 1H); 7.9 (s 1H); 7.72 (ddd 1H); 7.58 (dd 1H); 7.3 (ddd 1H); 4.95 (dd 1H); 4.7 (dd 1H); 4.3 (m 1H); 4 (dd 1H); 3.7 (m 3H); 3.32 (dd 1H) ppm Example No. 2

Following the procedure described in Example no. 1 and using 4-acetylpyridine, the intermediate cis(±)-2-(pyridin-4-yl)-2-(1,2,4-triazol-1-yl-methyl)-4-hydroxymethyl-1,3-dioxolane was obtained.

$^1$H-NMR (200 MHz):

δ (CDCl$_3$)=8.6 (d 2H); 8.1 (s 1H); 8.0 (s 1H); 7.2 (d 2H); 4.9 (t 1H); 4.5 (s 2H); 4.2 (m 1H); 3.8 (m 1H); 3.6 (m 1H); 3.1 (m 2H) ppm Example No. 3

Following the procedure described in Example no. 1 and using 3-acetylpyridine, the intermediate cis(±)-2-(pyridin-3-yl)-2-(1,2,4-triazol-1-yl-methyl)-4-hydroxymethyl-1,3-dioxolane was obtained.

$^1$H-NMR (200 MHz):

δ (CDCl$_3$)=8.55 (m 2H); 8.4 (s 1H); 7.9 (s 1H); 7.7 (m 1H); 7.2 (m 1H); 4.85 (t 1H); 4.65 (s 2H); 4.0 (m 1H); 3.8 (m 1H); 3.6 (m 1H); 3.25 (m 1H); 3.1 (m 1H) ppm Example No. 4

Following the procedure described in Example no. 1 and using 2-acetylthiazole, the intermediate cis(±)-2-(thiazol-2-yl)-2-(1,2,4-triazol-1-yl-methyl)-4-hydroxymethyl-1,3-dioxolane was obtained.

$^1$H-NMR (200 MHz):

δ (CDCl$_3$)=8.2 (d 1H); 7.9 (m 2H); 7.4 (d 1H); 5.05 (d 1H); 4.8 (m 1H); 4.45 (m 1H); 4.15 (t 1H); 3.85 (m 3H); 3.3 (dd 1H) ppm Example No. 5

3 g of *Pseudomonas cepacia* lipases (PCL) were added to a solution of 5 g of cis(±)2-(pyridin-2-yl)-2-(1,2,4-triazol-1-yl-methyl)-4-hydroxymethyl-1,3-dioxolane, obtained as described in Example no. 1, and 17 ml of vinyl acetate in 100 ml of dichloromethane. The suspension was stirred for seven days, any changes in the reaction being monitored by HPLC with a chiral column (Chiralcel OJ, eluent ethanol/n-hexane 55:45).

The enzyme was filtered out and the solution was concentrated and introduced into a silica gel column (eluent dichloromethane/methanol, 95:5). 1.5 g of cis(−)2-(pyridin-2-yl)-2-(1,2,4-triazol-1-yl-methyl)-4-hydroxymethyl-1,3-dioxolane were isolated.

([α]$_D^{25°\,C.}$=−13.6 (c=2.3; EtOH); ee=85%).

Example No. 6

4 g of cis(±)2-(pyridin-2-yl)-2-(1,2,4-triazol-1-yl-methyl)-4-acetoxymethyl-1,3-dioxolane, obtained from Example no. 5, partially enriched with cis(+) isomer, were hydrolysed with NaOH in methanol giving rise to 3 g of cis(+)2-(pyridin-2-yl)-2-(1,2,4-triazol-1-yl-methyl)-4-hydroxymethyl-1,3-dioxolane with an enantiomeric excess of 37%. The latter was dissolved in 80 ml of dichloromethane and 4 g of PCL and 15 ml of vinyl acetate were added to the solution. The suspension was stirred for 30 hours, any changes in the reaction being monitored by HPLC with a chiral column (Chiralcel OJ, eluent ethanol/n-hexane 55:45).

The enzyme was filtered out and the solution was concentrated and introduced into a silica gel column (eluent dichloromethane/methanol, 95:5). 1.24 g of cis(+)2-(pyridin-2-yl)-2-(1,2,4-triazol-1-yl-methyl)-4-acetoxymethyl-1,3-dioxolane were isolated. The ester was hydrolysed with NaOH in methanol and the residue was purified on a silica gel column (eluent dichloromethane/methanol, 97:3) giving rise to 1.05 g of cis(+)2-(pyridin-2-yl)-2-(1,2,4-triazol-1-yl-methyl)-4-hydroxymethyl-1,3-dioxolane ([α]$_D^{25°\,C.}$=+14.0 (c=2.1; EtOH); ee=82%).

(B) Preparation of the Intermediates of the Formula (IV)

Various intermediates of the formula (IV) may be obtained commercially (e.g. 4-{4-[4-(4-hydroxyphenyl)-piperazin-1-yl]phenyl}-2,4-dihydro-2-[(1,R/S)-1-methylpropyl]-3H-1,2,4-triazol-3-one; Nosch Labs, Hyderabad, India) or may be prepared in accordance with known procedures (c.f. for example U.S. Pat. No. 4,267,179). The individual enantiomers of the intermediates (IV) which contain a chiral centre may be prepared using specific chiral reactants as shown in the following Examples.

Example No. 7

A) 5 g of 4-toluenesulfonic acid (1,R)-1-methylpropyl ester were added to a suspension of 6 g of 4-{4-[4-(4-methoxyphenyl)-piperazin-1-yl]phenyl}-2,4-dihydro-3H-1,2,4-triazol-3-one and 1.12 g of KOH in 150 ml of DMSO. The reaction mixture was stirred at 40° C. for 4 days, after which the solution was poured into 400 ml of water and the precipitate was filtered out and dried. The solid was suspended in 200 ml of methylene chloride and the insoluble fraction was removed by filtration; the filtered solution was evaporated and the residue was purified on a silica gel column (eluent CH$_2$Cl$_2$/methanol, 98:2, vol./vol.), giving rise to 3.2 g of 4-{4-[4-(4-methoxyphenyl)-piperazin-1-yl]phenyl}-2,4-dihydro-2-[(1,S)-1-methylpropyl]-3H-1,2,4-triazol-3-one (yield 51%).

B) 3.2 g of 4-{4-[4-(4-methoxyphenyl)-piperazin-1-yl]phenyl}-2,4-dihydro-2-[(1,S)-1-methylpropyl]-3H-1,2,4-triazol-3-one obtained in the previous section were dissolved in 33 ml of 48% hydrobromic acid and the solution was refluxed for 6h. On completion, the mixture was cooled, the crystallised product was collected by filtration; the solid was dissolved in 100 ml of methanol/water (1:1, vol./vol.) and the solution was saturated by adding solid NaHCO$_3$. The suspension was diluted with 70 ml of water and extracted three times with 80 ml of methylene chloride. The combined organic phases were dehydrated and evaporated to dryness. The residue was suspended in 70 ml of tert.-butyl methyl ether and stirred for 15 minutes; the solid was filtered out, giving rise to 2.1 g of 4-{4-[4-(4-hydroxyphenyl)-piperazin-1-yl]phenyl}-2,4-dihydro-2-[(1,S)-1-methylpropyl]-3H-1,2,4-triazol-3-one (yield 73%).

$^1$H-NMR (200 MHz):

δ (DMSO-d$_6$)=8.88 (s 1H); 8.34 (s 1H); 7.5 (d 2H); 7.1 (d 2H); 6.88 (d 2H); 6.7 (d 2H); 4.12 (m 1H); 3.33 (m 4H); 3.1 (m 4H); 1.7 (m 2H); 1.3 (d 3H); 0.8 (t 3H)

Example No. 8

Following the procedure described in Example no. 7 and using 4-toluenesulfonic acid (1,S)-1-methylpropyl ester, the intermediate 4-{4-[4-(4-hydroxyphenyl)-piperazin-1-yl]phenyl}-2,4-dihydro-2-[(1,R)-1-methylpropyl]-3H-1,2,4-triazol-3-one (yield 73%) was obtained.

$^1$H-NMR (200 MHz):

δ (DMSO-d$_6$)=8.88 (s 1H); 8.34 (s 1H); 7.5 (d 2H); 7.1 (d 2H); 6.88 (d 2H); 6.7 (d 2H); 4.12 (m 1H); 3.33 (m 4H); 3.1 (m 4H); 1.7 (m 2H); 1.3 (d 3H); 0.8 (t 3H)

(C) Preparation of the Final Products of the Formula (I)

Example No. 9

A) Synthesis of cis(±)-[2-(pyridin-2-yl)-2-(1,2,4-triazol-1-yl-methyl)-1,3-dioxolan-4-ylmethyl]4-toluenesulfonate 2.72 g of cis(±)-2-(pyridin-2-yl)-2-(1,2,4-triazol-1-yl-methyl)-4-hydroxymethyl-1,3-dioxolane were dissolved in 8.16 ml of pyridine and the solution was cooled in an ice bath. 2.36 g of 4-toluenesulfonyl chloride were added in portions to the solution and, once addition was complete, the reaction mixture was adjusted to ambient temperature and stirred for approx. 2 hours.

The reaction mixture was then diluted with 100 ml of ethyl acetate and washed first with 50 ml of 5% NaHCO$_3$ and then with 50 ml of water.

The organic phase was dehydrated with Na$_2$SO$_4$ and evaporated to dryness. The crude product obtained in this manner was purified on a silica gel column (eluent ethyl acetate/methanol, 10:1, vol./vol.), giving rise to 3.34 g of cis(±) -[2-(pyridin-2-yl)-2-(1,2,4-triazol-1-ylmethyl)-1,3-dioxolan-4-ylmethyl]4-toluenesulfonate (yield 78%).

B) Synthesis of cis(±)-4-{4-[4-{2-(pyridin-2-yl)-2-(1H-1,2,4-triazol-1-ylmethyl)-1,3-dioxolan-4-yl-methoxy]phenyl}-1-piperazinyl]-phenyl}-2-(1-(R,S)methylpropyl)-2,4-dihydro-3H-1,2,4-triazol-3-one 0.818 g of potassium tert.-butylate were added to a solution of 2.835 g of 2,4-dihydro-4-{4-[4-(4-hydroxyphenyl)-1-piperazinyl]phenyl}-2-(1-(R,S)methylpropyl)-3H-1,2,4-triazol-3-one in 60 ml of DMF. After 5 minutes, a solution of 3 g of cis(±)-[2-(pyridin-2-yl)-2-(1,2,4-triazol-1-yl-methyl)-1,3-dioxolan-4-yl-methyl]4-toluenesulfonate, obtained in the previous section, in 60 ml of DMF was added. The reaction mixture was adjusted to 130° C. and stirred for 3 hours, after which the solvent was evaporated under reduced pressure and the residue was resuspended with 60 ml of 1N NaOH; the mixture was extracted three times with 120 ml of toluene. The combined organic phases were filtered and washed twice with 60 ml of 1N NaOH and then with 120 ml of 5% NaCl. The organic phase was dehydrated and evaporated under reduced pressure, the residue was suspended in 13.5 ml of methyl ethyl ketone and the suspension was stirred for one hour. On completion, the solid was recovered by filtration and dried, giving rise to 1.275 g of cis(±)-4-{4-[4-{4-[2-(pyridin-2-yl)-2-(1H-1,2,4-triazol-1-yl-methyl)-1,3-dioxolan-4-yl-methoxy]phenyl}piperazin-1-yl]-phenyl}-2-[(1,R/S)-1-methylpropyl]-2,4-dihydro-3H-1,2,4-triazol-3-one (yield 28%; m.p.=166-167° C.).

$^1$H-NMR (200 MHz):

δ (CDCl$_3$)=8.72 (d 1H); 8.22 (s 1H); 7.91 (s 1H); 7.75 (ddd 1H); 7.60 (m 2H); 7.37 (m 3H); 6.92 (m 6H); 4.82 (s 2H); 4.45 (m 1H); 4.3 (m 1H); 4.03 (dd 1H); 3.82 (m 2H); 3.78 (m 9H); 1.78 (m 2H); 1.39 (d 3H); 0.91 (t 3H)

Example No. 10

Following the procedure described in Example no. 9 and using cis(±)-2-(pyridin-4-yl)-2-(1,2,4-triazol-1-yl-methyl)-4-hydroxymethyl-1,3-dioxolane, obtained in Example no. 2, the product cis(±)-4-{4-[4-{4-[2-(pyridin-4-yl)-2-(1H-1,2,4-triazol-1-yl-methyl)-1,3-dioxolan-4-yl-methoxy]phenyl}-1-piperazinyl]-phenyl}-2-(1-(R,S)methylpropyl)-2,4-dihydro-3H-1,2,4-triazol-3-one was obtained (m.p.=168-172° C.).

$^1$H-NMR (200 MHz):

δ (CDCl$_3$)=8.65 (d 2H); 8.20 (s 1H); 7.95 (s 1H); 7.60 (s 1H); 7.45 (m 4H); 6.90 (m 5H); 6.75 (d 1H); 4.52 (s 2H); 4.3 (m 2H); 4.1 (m 1H); 3.85 (m 3H); 3.3 (m 8H); 1.75 (m 2H); 1.40 (d 3H); 0.90 (t 3H)

Example No. 11

Following the procedure described in Example no. 9 and using cis(±)-2-(pyridin-3-yl)-2-(1,2,4-triazol-1-yl-methyl)-4-hydroxymethyl-1,3-dioxolane, obtained in Example no. 3, the product cis(±)-4-{4-[4-{4-[2-(pyridin-3-yl)-2-(1H-1,2,4-triazol-1-yl-methyl)-1,3-dioxolan-4-yl-methoxy]phenyl}-1-piperazinyl]-phenyl}-2-(1-(R,S)methylpropyl)-2,4-dihydro-3H-1,2,4-triazol-3-one was obtained (m.p.=166-167° C.).

$^1$H-NMR (200 MHz):

δ (CDCl$_3$)=8.80 (s 1H); 8.65 (d 1H); 8.24 (s 1H); 7.92 (s 1H); 7.82 (d 1H); 7.62 (s 1H); 7.38 (m 3H); 6.99 (m 4H); 6.8 (d 2H); 4.56 (s 2H); 4.33 (m 2H); 3.38 (m 3H); 3.42 (m 9H); 1.78 (m 2H); 1.39 (d 3H); 0.90 (t 3H)

Example No. 12

Following the procedure described in Example no. 9 and using cis(±)-2-(thiazol-2-yl)-2-(1,2,4-triazol-1-yl-methyl)-4-hydroxymethyl-1,3-dioxolane, obtained in Example no. 4, the product cis(±)-4-{4-[4-{4-[2-(thiazol-2-yl)-2-(1H-1,2,4-triazol-1-yl-methyl)-1,3-dioxolan-4-yl-methoxy]phenyl}-1-piperazinyl]-phenyl}-2-(1-(R,S)methylpropyl)-2,4-dihydro-3H-1,2,4-triazol-3-one was obtained (m.p.=155° C. dec.).

$^1$H-NMR (200 MHz):

δ (CDCl$_3$)=8.2 (s 1H); 7.9 (m 2H); 7.61 (s 1H); 7.42 (m 3H); 6.99 (m 4H); 6.80 (d 2H); 4.90 (s 2H); 4.58 (m 1H); 4.25 (m 2H); 3.81 (m 2H); 3.38 (m 10H); 1.75 (m 2H); 1.37 (d 3H); 0.89 (t 3H)

Example No. 13

Proceeding as described in Example no. 9, the intermediate cis(−)2-(pyridin-2-yl)-2-(1,2,4-triazol-1-yl-methyl)-4-hydroxymethyl-1,3-dioxolane, obtained in Example no. 5, and the intermediate 4-{4-[4-(4-hydroxyphenyl)-piperazin-1-yl]phenyl}-2,4-dihydro-2-[(1,S)-1-methylpropyl]-3H-1,2,4-triazol-3-one, obtained in Example no. 7, were used to obtain cis(−)-4-{4-[4-{4-[2-(pyridin-2-yl)-2-(1H-1,2,4-triazol-1-yl-methyl)-1,3-dioxolan-4-yl-methoxy]phenyl}piperazin-1-yl]-phenyl}-2-[(1,S)-1-methylpropyl]-2,4-dihydro-3H-1,2,4-triazol-3-one.

Chiral HPLC [Chiralcel OJ (4.6×250 mm); eluent ethanol/hexane (75:25, vol./vol.); 0.6 ml/min.]: Rt=91.73 min.

Example No. 14

Proceeding as described in Example no. 9, the intermediate cis(+)2-(pyridin-2-yl)-2-(1,2,4-triazol-1-yl-methyl)-4-hydroxymethyl-1,3-dioxolane, obtained in Example no. 6, and the intermediate 4-{4-[4-(4-hydroxyphenyl)-piperazin-1-yl]phenyl}-2,4-dihydro-2-[(1,S)-1-methylpropyl]-3H-1,2,4-triazol-3-one, obtained in Example no. 7, were used to obtain cis(+)-4-{4-[4-{4-[2-(pyridin-2-yl)-2-(1H-1,2,4-triazol-1-yl-methyl)-1,3-dioxolan-4-yl-methoxy]phenyl}piperazin-1-yl]-phenyl}-2-[(1,S)-1-methylpropyl]-2,4-dihydro-3H-1,2,4-triazol-3-one.

Chiral HPLC [Chiralcel OJ (4.6×250 mm); eluent ethanol/hexane (75:25, vol./vol.); 0.6 ml/min.]: Rt=119.04 min.

Example No. 15

Proceeding as described in Example no. 9, the intermediate cis(−)-2-(pyridin-2-yl)-2-(1,2,4-triazol-1-yl-methyl)-4-hydroxymethyl-1,3-dioxolane, obtained in Example no. 5, and the intermediate 4-{4-[4-(4-hydroxyphenyl)-piperazin-1-yl]phenyl}-2,4-dihydro-2-[(1,R)-1-methylpropyl]-3H-1,2,4-triazol-3-one, obtained in Example no. 8, were used to obtain cis(−)-4-{4-[4-{4-[2-(pyridin-2-yl)-2-(1H-1,2,4-triazol-1-yl-methyl)-1,3-dioxolan-4-yl-methoxy]phenyl}piperazin-1-yl]-phenyl}-2-[(1,R)-1-methylpropyl]-2,4-dihydro-3H-1,2,4-triazol-3-one.

Chiral HPLC [Chiralcel OJ (4.6×250 mm); eluent ethanol/hexane (75:25, vol./vol.); 0.6 ml/min.]: Rt=68.28 min.

Example No. 16

Proceeding as described in Example no. 9, the intermediate cis(+)2-(pyridin-2-yl)-2-(1,2,4-triazol-1-ylmethyl)-4-hydroxymethyl-1,3-dioxolane, obtained in Example no. 6, and the intermediate 4-{4-[4-(4-hydroxyphenyl)-piperazin-1-yl]phenyl}-2,4-dihydro-2-[(1,R)-1-methylpropyl]-3H-1,2,4-triazol-3-one, obtained in Example no. 8, were used to obtain cis(+)-4-{4-[4-{4-[2-(pyridin-2-yl)-2-(1H-1,2,4-triazol-1- yl-methyl)-1,3-dioxolan-4-yl-methoxy]phenyl}piperazin-1-yl]-phenyl}-2-[(1,R)-1-methylpropyl]-2,4-dihydro-3H-1,2,4-triazol-3-one.

Chiral HPLC [Chiralcel OJ (4.6×250 mm); eluent ethanol/hexane (75:25, vol./vol.); 0.6 ml/min.]: Rt=79.31 mm.

Example No. 17

A) 0.1 g of cis(±)-[2-(pyridin-2-yl)-2-(1,2,4-triazol-1-yl-methyl)-1,3-dioxolan-4-yl-methyl]4-toluenesulfonate, obtained as described in section A) of Example no. 9, were dissolved in 4 ml of anhydrous methylene chloride and 48 mg of meta-chloroperbenzoic acid were added in portions to the solution which had been cooled to 0° C. The mixture was stirred at ambient temperature for 30 hours, after which the solvent was evaporated and the residue was purified on a silica gel column (eluent: gradient from ethyl acetate to ethyl acetate/methanol, 8:2, vol./vol.), giving rise to 100 mg of cis(±)-[2-(1-oxy-pyridin-2-yl)-2-(1,2,4-triazol-1-yl-methyl)-1,3-dioxolan-4-yl-methyl]4-toluenesulfonate (yield 62%).

B) Proceeding as described in section B) of Example no. 9 and using the activated intermediate obtained in the preceding section, cis(±)-4-{4-[4-{4-[2-(1-oxy-pyridin-2-yl)-2-(1H-1,2,4-triazol-1-yl-methyl)-1,3dioxolan-4-yl-methoxy]phenyl}piperazin-1-yl]-phenyl}-2-[(1,R/S)-1-methylpropyl]-2,4-dihydro-3H-1,2,4-triazol-3-one (m.p. .=206-210° C.) was obtained.

$^1$H-NMR (200 MHz):
δ (CDCl$_3$)=8.3 (d 1H); 8.25 (s 1H); 7.9 (s 1H); 7.65 (s 1H); 7.6 (d 1H); 7.45 (d 2H); 7.3 (m 2H); 7.05 (d 2H); 6.95 (d 2H); 6.85 (d 2H); 5.25 (dd 2H); 4.5 (m 1H); 4.40 (m 1H); 4.30 (m 1H); 4.10 (m 1H); 4.05 (m 1H); 3.95 (m 1H); 3.70 (m 1H); 3.4 (m 4H); 3.25 (m 4H); 1.70 (m 2H); 1.40 (d 3H); 0.90 (t 3H)

Example No. 18

Proceeding as described in Example no. 17 and using the activated intermediate cis(±)-[2-(pyridin-4-yl)-2-(1,2,4-triazol-1-yl-methyl)-1,3-dioxolan-4-ylmethyl]4-toluenesulfonate, obtained as described in Example no. 2, cis(±)-4-{4-[4-{4-[2-(1-oxy-pyridin-4-yl)-2-(1H-1,2,4-triazol-1-yl-methyl)-1,3-dioxolan-4-yl-methoxy]phenyl}piperazin-1-yl]phenyl}-2-[(1,R/S)-1-methylpropyl]-2,4-dihydro-3H-1,2,4-triazol-3-one (m.p.=213-216° C.) was obtained.

$^1$H-NMR (200 MHz):
δ (CDCl$_3$)=8.25 (s 1H); 8.15 (d 2H); 7.95 (s 1H); 7.60 (s 1H); 7.45 (d 2H); 7.35 (d 2H); 7.15 (d 2H); 6.90 (d 2H); 6.65 (d 2H); 4.5 (s 2H); 4.3 (m 2H); 4.1 (m 1H); 3.9 (m 3H); 3.35 (m 4H); 3.25 (m 4H); 1.8 (m 2H); 1.40 (d 3H); 0.90 (t 3H).

The invention claimed is:

1. A compound selected from the group consisting of the azole derivatives having the general formula

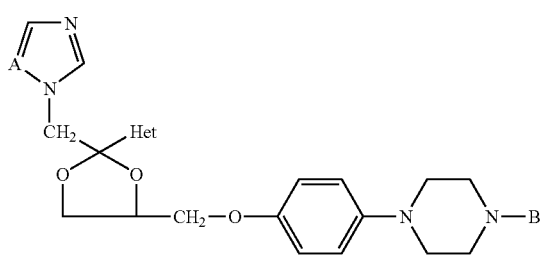

including the salts thereof with pharmaceutically acceptable acids, the N-oxide forms thereof and the sterochemical isomers thereof, where:

A is N or CH;
Het is an aromatic heterocyclic radical containing one or more O or N atoms, optionally substituted with one or more 5- or 6-membered aromatic rings;
B is an alkanoic residue containing from 1 to 6 carbon atoms or is a residue of the formula

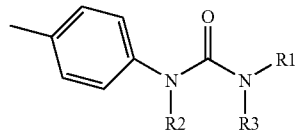

where:
R1 is hydrogen or a linear or branched alkyl residue containing from 1 to 6 carbon atoms and optionally substituted in one or more positions by hydroxyl groups;
R2 and R3, taken separately, are hydrogen or an alkyl with 1-4 carbon atoms or, taken together, are a divalent radical of the formula —CH═N—, —N═CH—, —CH═CH—, —CH2—CH2—.

2. A compound according to claim 1 wherein A) is a nitrogen atom.

3. A compound according to claim 1 wherein Het is selected from among: pyridine, pyridazine, pyrazine, pyrimidine, oxazole, pyrrole, pyrazole, imidazole, triazole and any corresponding fusion derivatives having two or more rings or with one or more benzene rings.

4. A compound according to claim 1 wherein B) is formyl, acetyl or propanoyl.

5. A compound according to claim 1 wherein B has the formula:

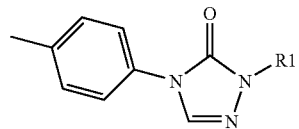

where R1 is hydrogen or a linear or branched alkyl residue containing from 1 to 6 carbon atoms and optionally substituted in one or more positions by hydroxyl groups.

6. A compound selected from the group consisting of cis-4-{4-[4-{4-[2-(2-pyridinyl)-2-(1 H-1,2,4-triazol- 1 -yl-methyl)- 1 ,3-dioxolan-4-yl-methoxy]phenyl}- 1-piperazinyl]-phenyl}-2-( 1-methyl)-propyl-2,4-dihydro-3H-1,2,4-triazol-3-one, the salts thereof with pharmaceutically acceptable acids and the stereochemical isomers thereof.

7. A pharmaceutical composition containing a compound according to claim 1, alone or in combination with at least one other active ingredient, together with one or more pharmaceutically acceptable excipients and/or auxiliary substances.

8. A process for the production of a compound according to claim 1 in which a compound of the formula III Formula (III)

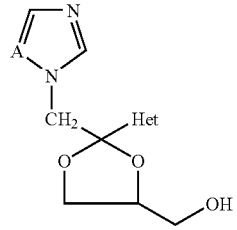

where: A is N or CH and Het is an aromatic heterocyclic radical containing one or more O or N atoms, optionally substituted with one or more 5- or 6-membered aromatic rings;

is reacted with a compound of the formula

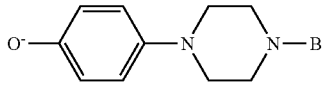

Formula (IV)

where: B is an alkanoic residue containing from 1 to 6 carbon atoms or is a residue of the formula

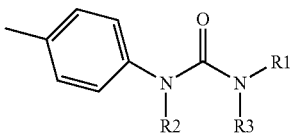

where: R1 is hydrogen or a linear or branched alkyl residue containing from 1 to 6 carbon atoms and optionally substituted in one or more positions by hydroxyl groups; R2 and R3, taken separately, are hydrogen or an alkyl with 1-4 carbon atoms or, taken together, are a divalent radical of the formula —CH=N—, —N=CH—, —CH=CH—, —CH2—CH2—.

* * * * *